United States Patent
Plasson et al.

(10) Patent No.: US 11,399,546 B2
(45) Date of Patent: Aug. 2, 2022

(54) **THERAPEUTIC OR NON-THERAPEUTIC USE OF PROTOZOANS OF THE *WILLAERTIA* GENUS AS A FUNGISTATIC AND/OR FUNGICIDE**

(71) Applicant: AMOEBA, Chassieu (FR)

(72) Inventors: Fabrice Plasson, Lyons (FR); Mouh Oulhadj Mameri, Vaulx en Velin (FR)

(73) Assignee: AMOEBA, Chassieu (FR)

(*) Notice: Subject to any disclaimer, the term of this patent is extended or adjusted under 35 U.S.C. 154(b) by 95 days.

(21) Appl. No.: 16/637,532

(22) PCT Filed: Aug. 9, 2018

(86) PCT No.: PCT/FR2018/052040
§ 371 (c)(1),
(2) Date: Feb. 7, 2020

(87) PCT Pub. No.: WO2019/030459
PCT Pub. Date: Feb. 14, 2019

(65) Prior Publication Data
US 2020/0390826 A1    Dec. 17, 2020

(30) Foreign Application Priority Data
Aug. 10, 2017 (FR) .................. 17 57644

(51) Int. Cl.
*A01N 63/00* (2020.01)
*A61K 35/68* (2006.01)

(52) U.S. Cl.
CPC .......... *A01N 63/00* (2013.01); *A61K 35/68* (2013.01)

(58) Field of Classification Search
CPC .................. A01N 63/00; A61K 35/68

USPC ........................................ 424/93.1
See application file for complete search history.

(56) References Cited

U.S. PATENT DOCUMENTS

| | | | |
|---|---|---|---|
| 8,168,167 B2* | 5/2012 | Bodennec | A01N 63/00 424/93.1 |
| 2011/0300106 A1 | 12/2011 | Filutowicz et al. | |
| 2016/0249624 A1* | 9/2016 | Plasson | C02F 1/50 424/93.1 |
| 2019/0231827 A1* | 8/2019 | Baker | A01N 63/00 |

FOREIGN PATENT DOCUMENTS

| | | |
|---|---|---|
| CN | 104093313 A | 10/2014 |
| CN | 104302182 A | 1/2015 |
| RU | 2 575 998 C1 | 2/2016 |
| RU | 2575 999 C2 | 2/2016 |
| WO | 2008/043969 A2 | 4/2008 |
| WO | 2013/079722 A1 | 6/2013 |
| WO | 2013/092897 A1 | 6/2013 |
| WO | 2015/059411 A1 | 4/2015 |

OTHER PUBLICATIONS

Steenbergen et al: "Interaction of Blastomyces dermatitidis, Sporothrix schenckii, and Histoplasma capsulatum with Acanthamoeba castellanii", Infection and Immunity, vol. 72, No. 6, pp. 3478-3488, Jun. 1, 2004.

Grueb et al: "Microorganisms Resistant to Free-Living Amoebae", Clinical Microbiology Review., vol. 17, No. 2, pp. 413-433, Apr. 1, 2004.

* cited by examiner

*Primary Examiner* — Jennifer M. H. Tichy
(74) *Attorney, Agent, or Firm* — WCF IP

(57) ABSTRACT

The invention relates to a therapeutic or non-therapeutic use of protozoans, for examples protozoans of the *Willaertia magna* amoeba species, as a fungistatic and/or fungicide.

7 Claims, 3 Drawing Sheets

US 11,399,546 B2

THERAPEUTIC OR NON-THERAPEUTIC USE OF PROTOZOANS OF THE WILLAERTIA GENUS AS A FUNGISTATIC AND/OR FUNGICIDE

TECHNICAL FIELD OF THE INVENTION

The present invention relates to the use of protozoa of the *Willaertia* genus, in particular *Willaertia magna*, as as fungistatic and/or fungicide.

CONTEXT

Fungi (yeasts and molds) are responsible for numerous diseases which affect plants, animals and human beings.

Numerous fungicides have thus been developed for eliminating fungi or limiting the development thereof, and consequently treating and/or preventing the diseases induced by fungi.

On the other hand, the use of these compounds is often not optimal, whether in terms of efficacy or in terms of toxicity to human beings or the environment.

Indeed, the agricultural or non-agricultural bulk use of pesticides or of chemical antifungals raises numerous health and ecological problems. In environmental terms, a cross-contamination of soils and water tables with the molecules contained in phytosanitary products has been observed. These pollutants can be responsible for disruptions in the ecosystems contaminated, by virtue of their potential toxicological effects on the non-targeted organisms. In addition to the ecological risks, the dangers associated with the use of and exposure to pesticides have also been well demonstrated and are the subject of a warning by the World Health Organization (WHO). Regarding the treatment of mycoses, it is necessary to provide an antimycotic compound which is nontoxic to human beings. Furthermore, the bulk use of these compounds results in the appearance of strains resistant to these products. The evolution of populations results in the end in decreases in the efficacy of the products, which can go as far as total loss of efficacy.

Increased awareness of the ecological and health risks caused by the bulk use of chemical pesticides has thus contributed to promoting, for several years, the development of a demand for antifungal products of natural origin, the toxicological and environmental impact of which is lower. These products that are less harmful to human beings and their environment also have the advantage of a simplified use, since they benefit from reduced regulation.

There is thus a considerable need for the development of new broad-spectrum natural fungicide compositions which are both efficacious and simple to use, and the production costs of which are controlled.

It would also be advantageous for such compositions to be able to act on spores, in order to have optimal efficacy.

SUMMARY

In this context, the inventors have demonstrated, entirely unexpectedly, that the protozoa of the *Willaertia* genus, and in particular the protozoa of the *Willaertia magna* ameba species in live form and/or in dead form and/or in cell lysate form, have fungistatic and/or fungicidal activity, in particular by acting on the spores.

A first aspect of the present disclosure is the non-therapeutic use of protozoa of the *Willaertia* genus, for example of the *Willaertia magna* species, in live or dead form, and/or in cell lysate form, as a fungistatic and/or fungicide.

A second aspect of the present disclosure is the use of protozoa of the *Willaertia* genus, for example of the *Willaertia magna* species, in live and/or dead form and/or in cell lysate form, for use thereof as an antimycotic medicament.

A third aspect of the present disclosure is a phytopharmaceutical product comprising an effective amount of protozoa of the *Willaertia magna* species, in live and/or dead form and/or in cell lysate form.

A fourth aspect is a pharmaceutical product comprising an effective amount of protozoa of the *Willaertia magna* species, in live and/or dead form and/or in cell lysate form.

According to the present disclosure, the protozoa of the *Willaertia* genus, in particular of the *Willaertia magna* genus, in live and/or dead form and/or in cell lysate form, can be used preventively or curatively.

The protozoa of the *Willaertia magna* species, in live or dead form, can be used alone or, advantageously, in combination with other protozoa, and in particular protozoa of the *Solumitris* ameba genus, Cercozoa protozoa of the *Cercomonas* genus or Cercozoa protozoa of the *Paracercomonas* genus.

Preferably, the protozoa used in the context of the present disclosure correspond to the *Willaertia magna* strain deposited on Aug. 21, 2006, under the number PTA-7824 at the ATCC or to the *Willaertia magna* strain deposited on Aug. 21, 2006, under the number PTA-7825 at the ATCC, these two strains having been initially deposited in the names of the CENTRE NATIONAL DE LA RECHERCHE SCIENTIFIQUE (CNRS) [French National Center for Scientific Research]—3 rue Michel Ange—75794 PARIS CEDEX 16/France and UNIVERSITE LYON 1 CLAUDE BERNARD—43 Boulevard du 11 Novembre 1918-69622 VILLEURBANNE Cedex/France. Said deposited strains are also described in the publication of PCT international application WO2008/043969.

As used in the context of the present disclosure, the terms "plant" and "plants" denote equally whole plants and the parts isolated from these plants, such as the leaves, fruits, flowers, grains, seeds, trunk, roots, stems.

As used in the context of the present disclosure, the term "fungus" refers to single-cell or multicellular fungi, including yeasts and molds, in spore form or in mycelium form.

As used in the context of the present disclosure, the term "phytopharmaceutical product" denotes a preparation or a mixture of substances that is intended:

to protect plants against one or more pest organisms,
and/or to prevent the action of plant-pest organisms,
and/or to exert an action on the vital processes of plants (insofar as they are not nutritive substances),
and/or to ensure the preservation of plant products.

As used in the context of the present disclosure, the term "live form" denotes the metabolically active vegetative form of the protozoan.

As used in the context of the present disclosure, the term "dead form" denotes a metabolically inactive form of the protozoan, which has been inactivated by a mechanical, physical, thermal or chemical process, for example osmotic shock, heat shock, by ultrasound, or else under mechanical stress of centrifugation type for example. The "dead form" can contain whole dead cells, of the microorganism, or cell lysate, or a mixture of whole dead cells and of cell lysate. A lysate commonly denotes a material obtained as a result of the destruction or dissolution of biological cells by a phenomenon of cell lysis type, thus causing the release of the intracellular biological constituents naturally contained in the cells of the microorganism in question. For the purposes of the present invention, the term "dead form" is used without distinction to denote the dead cells of *Willaertia*, all of the lysate obtained by lysis of *Willaertia* or only a fraction thereof.

The distinction between live cells, dead cells and lysate can in particular be carried out by microscopic observation with staining using a non-viability label such as Trypan blue (CAS: 72-57-1) which labels the dead cells.

The non-therapeutic use has, in particular, multiples applications:

- for combating the proliferation of the parasitic fungi of plants, preferably for the treatment of fungal diseases of vine, of cereals, of potatoes, of fruit trees and of market garden crops, even more preferentially for the treatment of fungal diseases chosen from vine powdery mildew, vine downy mildew, cereal *septoria* disease and fusaria disease, cereal net blotch, potato downy mildew and early blight, apple tree scab, *Sclerotinia* stem rot of rape and vegetable crops and a combination thereof;
- for disinfecting the networks (other than the cooling towers) of air treatment facilities;
- for combating fungal contaminations and/or the formation of fungal biofilms in food products, food product transformation/production equipment, food product transformation/production factories, surfaces that come into contact with food products;
- for combating fungal contaminations and/or the formation of fungal biofilms in cosmetic products, cosmetic product transformation/production equipment, cosmetic product transformation/production factories, surfaces that come into contact with cosmetic products.

The use as an antimycotic medicament finds in particular application in the treatment of infections caused by fungi chosen from *Aspergillus, Candida, U. botrytis, A. niger, P. variotii, A. alternata*, and a combination thereof, preferably *Candida*, even more preferentially *Candida albicans*.

The invention also finds application in the treatment of nosocomial diseases caused by fungi, in particular respiratory pathologies.

Preferably, the protozoa of the *Willaertia* genus, in particular of the *Willaertia magna* species, in live or dead form (in particular in cell lysate form), or a mixture of live and dead forms, are used for combating a fungus chosen from the division *Ascomycota*, more preferentially from the class sordariomycetes, eurotiomycetes, dothideomycetes, saccharomycetes, leotiomycetes, oomycetes and a combination thereof, even more preferentially from the *Botrytis, Erysiphe, Fusarium, Penicillium, Plasmopara, Phytophthora, Chaetomium, Trichoderma, Aspergillus, Alternaria, Candida, Ulocladium, Epicoccum* and *Cladosporium* genera and a combination thereof and more preferably from *B. cinerea, E. necator, F. solani, C. globosum, P. chrysogenum, P. expansum, P. viticola, P. infestans, T viride, T harzianum, A. fumigatus, A. alternata, A. flavus, P. variotii, A. niger, C. albicans, U. botrytis, E. nigrum, B. cinerea, P. roqueforti, C. cladosporioides, E. chevalieri, A. pullulans* and a combination thereof.

In one particular embodiment, the protozoa of the *Willaertia magna* species are used in live form, or in dead form (in particular in cell lysate form), or as a mixture of live and dead forms. In one particular embodiment, the mixture used comprises 50% or more of protozoa in dead form, in particular in cell lysate form, for example 60% or more, 70% or more, 80% or more, 90% or more, 95% or more of protozoa in dead form (relative to the number of total protozoa before inactivation), in particular in cell lysate form.

In one particular embodiment, the protozoa of the *Willaertia magna* species, in live form or in dead form or in cell lysate form, or as a mixture of live forms, and/or of dead and/or cell lysate forms, are used for combating fungal diseases affecting plants. Preferably, the plants are chosen from grasses, dicotyledons, annual, biannual and perennial plants, vegetable plants or harvested vegetables, fruit plants or trees or harvested fruits, cereals, oil-yielding plants, protein-yielding plants, ligneous plants, and are in particular chosen from plants or products derived from potato, beetroot, sugar cane, tobacco, vine, wheat, rape, barley, rice, corn, sorghum, millet, soya, bean, tomato, cucumber, lettuce, strawberry, apple tree, pear tree, citrus fruits, banana, pineapple, peach, apricot tree, cherry tree, walnut tree and hazelnut tree.

In one particular embodiment, the protozoa of the *Willaertia magna* species, in live form or in dead form or in cell lysate form, or as a mixture of live forms, and/or of dead and/or cell lysate forms, are used for combating fungi affecting surfaces, materials, pieces of equipment and/or ventilation systems.

In one particular embodiment, the protozoa of the *Willaertia magna* species, in live form or in dead form or in cell lysate form, or as a mixture of live forms, and/or of dead and/or cell lysate forms, are used for combating fungi affecting human or animal health.

In another particular embodiment, the protozoa of the *Willaertia* genus, in particular of the *Willaertia magna* species, in live form or in dead form or in cell lysate form, or as a mixture of live forms, and/or of dead and/or cell lysate forms, are used for combating *F. solani* for the treatment of fungal diseases of plants (cereals and corn).

In another particular embodiment, the protozoa of the *Willaertia* genus, in particular of the *Willaertia magna* species, in live form or in dead form or in cell lysate form, or as a mixture of live forms, and/or of dead and/or cell lysate forms, are used for combating *C. globosum* for the treatment of fungal diseases of plants, preferably affecting cereals or rice, or for the treatment of contamination of cellulose-based products such as paper and construction materials.

In another particular embodiment, the protozoa of the *Willaertia magna* species, in live form or in dead form or in cell lysate form, or as a mixture of live forms, and/or of dead and/or cell lysate forms, are used for combating *P. viticola* for the treatment of fungal diseases of plants, preferably affecting vine.

In another particular embodiment, the protozoa of the *Willaertia magna* species, in live form or in dead form or in cell lysate form, or as a mixture of live forms, and/or of dead and/or cell lysate forms, are used for combating *P. infestans* for the treatment of fungal diseases of plants, preferably affecting potato.

In another particular embodiment, the protozoa of the *Willaertia* genus, in particular of the *Willaertia magna* species, in live form or in dead form or in cell lysate form, or as a mixture of live forms, and/or of dead and/or cell lysate forms, are used for combating molds of the *Penicillium* genus, such as *P. chrysogenum*, of the *Aspergillus* genus, such as *Aspergillus niger*, or of the *Cladosporium* genus, such as *Cladosporium cladosporioides*, for the treatment of contaminations of interior environments such as walls, materials, pieces of equipment and ventilation systems, etc.

In another particular embodiment, the protozoa of the *Willaertia* genus, in particular of the *Willaertia magna* species, in live form or in dead form or in cell lysate form, or as a mixture of live forms, and/or of dead and/or cell lysate forms, are used for combating *T. viride* and/or *T. harzianum* for the treatment of contaminations of food products and interior environments such as walls, materials, pieces of equipment and ventilation systems, etc.

In another particular embodiment, the protozoa of the *Willaertia* genus, in particular of the *Willaertia magna* species, in live form or in dead form or in cell lysate form, or as a mixture of live forms, and/or of dead and/or cell lysate forms, are used for combating *A. fumigatus* for the treatment of nosocomial diseases, in particular respiratory pathologies.

In another particular embodiment, the protozoa of the *Willaertia* genus, in particular of the *Willaertia magna* species, in live form or in dead form or in cell lysate form, or as a mixture of live forms, and/or of dead and/or cell lysate forms, are used for combating *A. alternata* for the treatment of fungal diseases of plants, preferably potato early blight, or the treatment of skin lesions, mycoses and infections of the upper respiratory tract in human beings.

In another particular embodiment, the protozoa of the *Willaertia* genus, in particular of the *Willaertia magna* species, in live form or in dead form or in cell lysate form, or as a mixture of live forms, and/or of dead and/or cell lysate forms, are used for combating *P. variotii* for the treatment of fungal contaminations and/or the formation of fungal biofilms in food products, preferably cereals, or for the treatment of mycoses, pneumonia, sinusitis in human beings.

In another particular embodiment, the protozoa of the *Willaertia* genus, in particular of the *Willaertia magna* species, in live form or in dead form or in cell lysate form, or as a mixture of live forms, and/or of dead and/or cell lysate forms, are used for combating *A. niger* for the treatment of fungal contaminations and/or the formation of fungal biofilms in food products, interior environments such as walls, materials, pieces of equipment and ventilation systems, etc., or for the treatment of inner ear mycoses or pulmonary aspergillosis in human beings.

In another particular embodiment, the protozoa of the *Willaertia* genus, in particular of the *Willaertia magna* species, in live or dead form, are used for combating *C. albicans* for the treatment of mycoses in human beings.

In another particular embodiment, the protozoa of the *Willaertia* genus, in particular of the *Willaertia magna* species, in live or dead form, are used for combating *U. botrytis* for the treatment of fungal diseases of plants, the treatment of fungal contaminations and/or the formation of fungal biofilms in food products and for the treatment of onycomycosis.

In another particular embodiment, the protozoa of the *Willaertia* genus, in particular of the *Willaertia magna* species, in live or dead form, are used for combating *E. nigrum* or *A. pullulans* for the treatment of fungal contaminations and/or the formation of fungal biofilms in food products or cosmetics or of the contamination of interior environments such as walls, materials, pieces of equipment and ventilation systems, etc.

In another particular embodiment, the protozoa of the *Willaertia* genus, in particular of the *Willaertia magna* species, in live or dead form, are used for combating *A. flavus, P. roqueforti, B. cinerea, C. cladosporioides* or *E. chevalieri* for the treatment of fungal contaminations and/or the formation of fungal biofilms in food products or cosmetics.

The present disclosure is also directed toward a phytopharmaceutical composition comprising an effective amount of protozoa of the *Willaertia magna* species, in live form or in dead form or in cell lysate form, or as a mixture of live forms, and/or of dead and/or cell lysate forms.

In one particular embodiment, the phytopharmaceutical composition contains an effective amount of protozoa of the *Willaertia magna* species, in cell lysate form.

In one particular embodiment, the phytopharmaceutical composition also comprises one or more formulating agents, in particular water, and, where appropriate, one or more additional active adjuvants.

In one particular embodiment, the phytopharmaceutical composition is a composition having a solid dry formulation, preferably in dehydrated or freeze-dried form. The phytopharmaceutical composition in dry form is intended to be reconstituted with a reconstitution solvent before use so as to be ready to use. The reconstitution solvent is preferably water.

In another particular embodiment, the phytopharmaceutical composition is a composition having a concentrated liquid formulation. The phytopharmaceutical composition in concentrated liquid form is intended to be diluted with a dilution solvent before use so as to be ready to use. The dilution solvent is preferably water.

In another particular embodiment, the phytopharmaceutical composition is a composition having a liquid formulation that is directly ready to use.

The phytopharmaceutical composition described above, in its final ready-to-use form, can be applied to plants in various ways and according to various treatment programs. In particular, the phytopharmaceutical composition can be applied before or after harvesting on the leaves, the soil, the flowers, the branches, the stems, the trunk, the roots and/or the fruits. The phytopharmaceutical composition is preferably applied by spraying. The phytopharmaceutical composition can also be applied in the form of a mixture with other phytopharmaceutical products, with fertilizer, with watering water, or the like.

For the non-therapeutic uses, the protozoa of the *Willaertia magna* species, in live or dead form, may be directly brought into contact on pieces of transformation/production equipment and surfaces that come into contact with food products or cosmetics, or on the plants to be treated. The treatment can be carried out for example by spraying, for example in the form of an aqueous aerosol solution. Such protozoa may thus also be used in combination with other disinfecting and/or pesticide agents.

The present disclosure is also directed toward a pharmaceutical composition comprising an effective amount of the protozoa of the *Willaertia magna* species, in live form or in dead form or in cell lysate form, or as a mixture of live forms, and/or of dead and/or cell lysate forms, as antimycotics, and a pharmaceutically acceptable carrier. Said pharmaceutical composition may in particular be a dressing comprising an active substance, a poultice, a medicated plaster, a gel, a paste, a lotion, a foam, an oil, an emulsion, aqueous solution, aqueous suspension, cream, ointment, powder or spray to be applied on the skin or the mucous membranes.

For the use as an antimycotic medicament, the protozoa, in particular of the *Willaertia magna* species, in live form or in dead form or in cell lysate form, or as a mixture of live forms, and/or of dead and/or cell lysate forms, may be topically applied on the lesions on the skin or the mucous membranes (for example in the form of a cream, ointment, spray or powder to be applied on the skin or the mucous membranes, typically the vaginal or anal mucous membranes).

The disclosure is also directed toward a pharmaceutical composition comprising an effective amount of the protozoa as antimycotics and a pharmaceutically acceptable carrier. Said pharmaceutical composition may in particular be a dressing comprising an active substance, a poultice, a medicated plaster, a gel, a paste, a lotion, a foam, an oil, an emulsion, aqueous solution, aqueous suspension, cream, ointment, powder or spray to be applied on the skin or the mucous membranes.

Another subject of the present disclosure is a method for combating the proliferation of fungi, with the exception of the treatment methods applied to the human or animal body, comprising a step of bringing protozoa of the *Willaertia magna* species, in live form or in dead form or in cell lysate form, or as a mixture of live forms, and/or of dead and/or cell lysate forms, into contact with said fungi.

EXAMPLES

Figure 1:
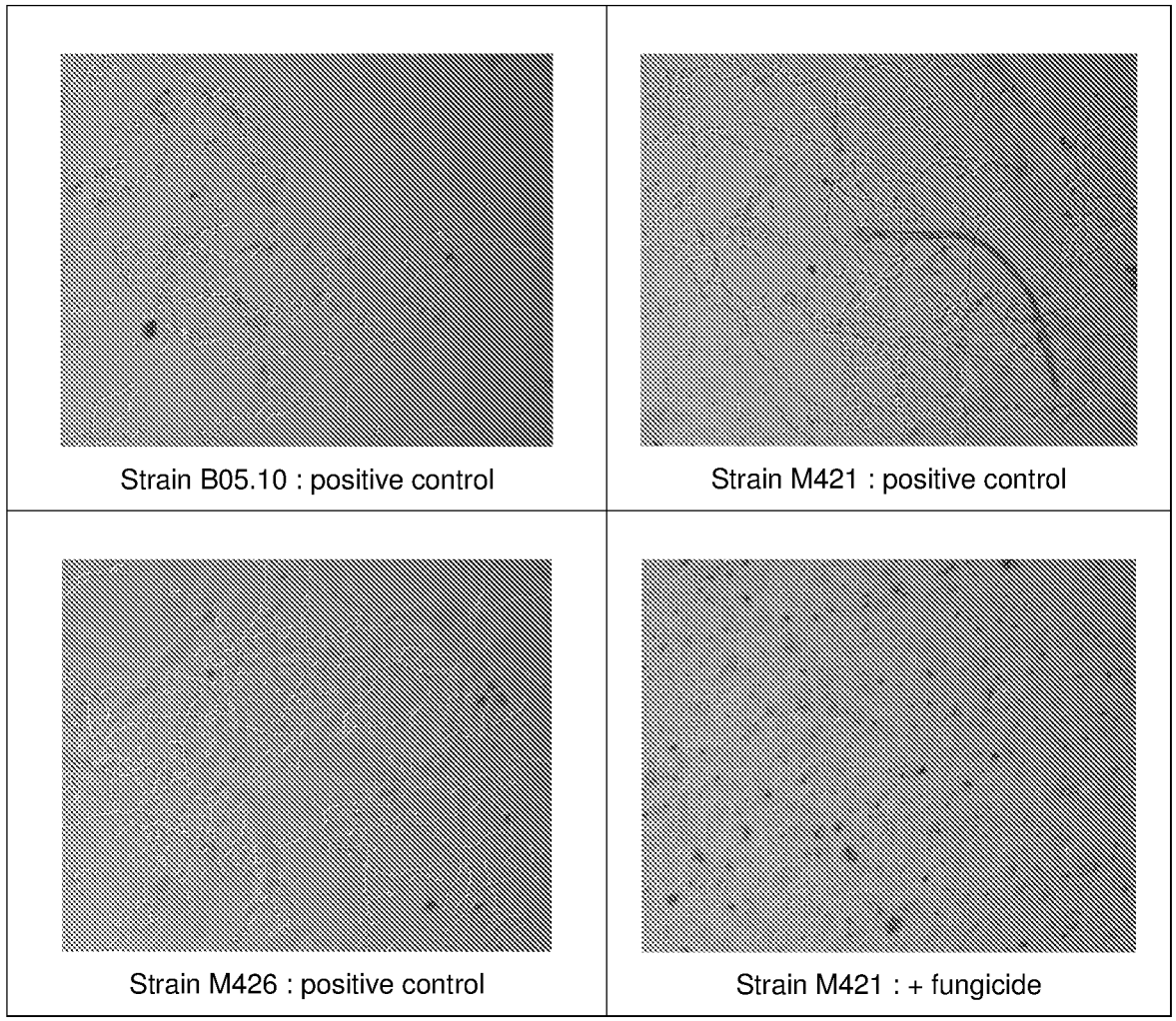
FIG. 1: Effect of the amebae on the germination of *B. cinerea*. Tests in a microplate in the presence of the *B. cinerea* spores without amebae. Observation after 24 H of incubation. Sensitive strains: B05.10 and M421. Resistant strain: M426. (respiration-inhibiting fungicide)

The examples hereinafter make it possible to illustrate the invention but are not limiting in nature.

Example 1: qPCR Analysis of the Fungal DNA of the Fungus—*Willaertia* Interactions on 19 Strains The interaction tests on 19 strains of fungi (table 1) were carried out by bringing the spores into contact with the "*Willaertia magna*" ameba reference ATCC PTA-7824 according to an ameba/spore ratio=10 amebae/spores, in 24-well plates.

In a first plate, spores alone of each strain were incubated under the same conditions (in 2 ml of MEAc). After 3 H of contact, the solution is centrifuged at 14 000 rpm for 5 minutes. The supernatant is then removed and the pellet taken up in 200 µl for the DNA extraction.

For the tests at 24 H carried out in a second plate, the supernatant is directly removed from the well after 24 hours and the "spores-amebae mixtures" are taken up in 200 µl in order to extract the DNA. Monitoring by microscopic observation is performed at each step. A DNA extraction is carried out on the samples (200 µl) using the "NucleoSpin plant II—Macherey-Nagel" kit according to the manufacturer's instructions after a milling step with fine sand.

The qPCR amplification of the DNA of the fungi alone and of the *Willaertia*-fungi complexes was carried out on a CFX96-Biorad instrument. The quantification is carried out in a final volume of 20 µl containing 5 µl of DNA, the primers (300 nM) and 10 µl of SybrGreen-Mix. The following program was used: a step of denaturation at 95° C. for 10 minutes with a step of amplification at "95° C. for 15 seconds+60° C. for 1 minute" of 35 cycles.

The tests carried out on the 19 strains of fungi are carried out according to the protocol validated in the preceding step. The plates are observed under a microscope before launching the molecular analysis. The results are qPCR curves obtained in triplicate for each condition (spores-3 H, spores-24 H, spore-ameba3 H and spore-ameba24 H). Given that the qPCR analysis uses universal primers, a range of the *P. chrysogenum* fungus was used to approximately estimate the amount of DNA amplified for each test. These data make it possible to evaluate the passage from the spore stage to the mycelium in the controls without ameba and also the degree of inhibition of the germination in the presence of the amebae.

Results and Conclusion

TABLE 1

Difference in qPCR amplification between the tests carried out on the spores alone (difference between 3 and 24 hours) and the spores undergoing interaction with the amebae after 24 H of contact. ΔCq (3 H-24 H): difference in number of cycles between the spores at 3 H and 24 H. ΔCq (T24 H-*Willaertia*24 H): difference in number of cycles between the spores alone (T24 H) and in presence of amebae (Amebae 24 H) after 24 h of incubation.

| Strain | ΔCq (3 H-24 H) | ΔCq (T24 H- *Willaertia* 24 H)* |
|---|---|---|
| *F. solani* | 3.3 | −4.1 |
| *C. globosum* | 7.6 | −3.8 |
| *P. chrysogenum* | 8.4 | −7.0 |
| *T. viride* | 13.3 | −12.9 |
| *T. harzianum* | 9.3 | −8.7 |
| *A. fumigatus* | 7.4 | −8.7 |
| *A. alternata* | 3.4 | −3.3 |
| *A. flavus* | 4.5 | −9.3 |
| *P. variotii* | 6.2 | −6.6 |
| *A. niger* | 8.92 | −9.63 |
| *C. albicans* | 10.7 | −3.3 |
| *U. botrytis* | 4.0 | −5.0 |
| *E. nigrum* | 0.1 | −4.6 |
| *B. cinerea* | 4.9 | −6.2 |
| *C. herbarum* | 0.9 | −0.8 |
| *P. roqueforti* | 6.4 | −13 |
| *C. cladosporioides* | 12.0 | −11.1 |
| *E. chevalieri* | 1.9 | −4.5 |
| *A. pullulans* | 7.7 | −7.1 |

*the values of ΔCq (T24 H-*Willaertia*24 H) are negative since the values of Cq corresponding to the "fungus-ameba 24 H" tests (low fungal biomass) are greater than those of the control tests at 24 H (high biomass).

The qPCR analysis made it possible to quantify the fungal biomass and to distinguish the stages of development of the fungi and to show the fungistatic and/or fungicidal effect on 19 treated strains with very significant differences. The difference in number of Cq cycles between the two tests with and without amebae is very significant and, in certain cases, exceeds 10 cycles. These results reflect the presence of a very low fungal biomass in the presence of the amebae after 24 H of incubation following the inhibition of the spore germination. The difference between the spore stage at 3 H and the mycelium developed after 24 H is clearly observed by the difference in amplification between the spores at 3 H and 24 H on tested strains. The qPCR results perfectly reflect the visual observations carried out under a microscope for developing this protocol.

Example 2: Study of the Effect of *Willaertia magna* on the Growth of *Botrytis cinerea*

Principle: the tests carried out are based on the tests used in the laboratory to evaluate the efficacy of conventional fungicidal molecules. The effect of the *Willaertia magna* ameba (strain ATCC PTA-7824) on the germination of the *B. cinerea* spores is analyzed by bringing various concentrations of amebae into contact with spores of the fungus. After 24 hours of incubation, the germination of the *B. cinerea* spores in the presence of ameba is compared to the control without amebae.

Protocol: the *B. cinerea* strains are maintained on culture medium (based on oat flakes) under alternating day-UV light (12 H/12 H) at 21° C. The strains have phenotypes sensitive or resistant to a fungicide belonging to the cell respiration inhibitors. The references of the strains tested are: strain B05.10 (sensitive), M421 (sensitive isolated from the field) and M426 (resistant isolated from the field). In order to test the effect of the *Willaertia magna* ameba on the germination of *B. cinerea* conidia, the spores of the fungus are incubated with various concentrations of amebae. In a 96-well plate, 500 *B. cinerea* spores are brought int contact with $5\times10^2$ and $5\times10^4$ amebae per well in a final volume of 50 µl. The amebae tested are prepared in culture medium (MC).

The following controls are also prepared under the same conditions:
- *B. cinerea* spores in a YBA liquid culture medium
- *B. cinerea* spores in culture medium (MC)
- *B. cinerea* spores with the respiration-inhibiting fungicide Each condition is tested in triplicate. The plates are incubated in the dark at 21° C. for 24 H or 48 H. The germination of the *B. cinerea* conidia is observed under an inverted microscope and a series of photos is taken for each condition.

Figure 2:
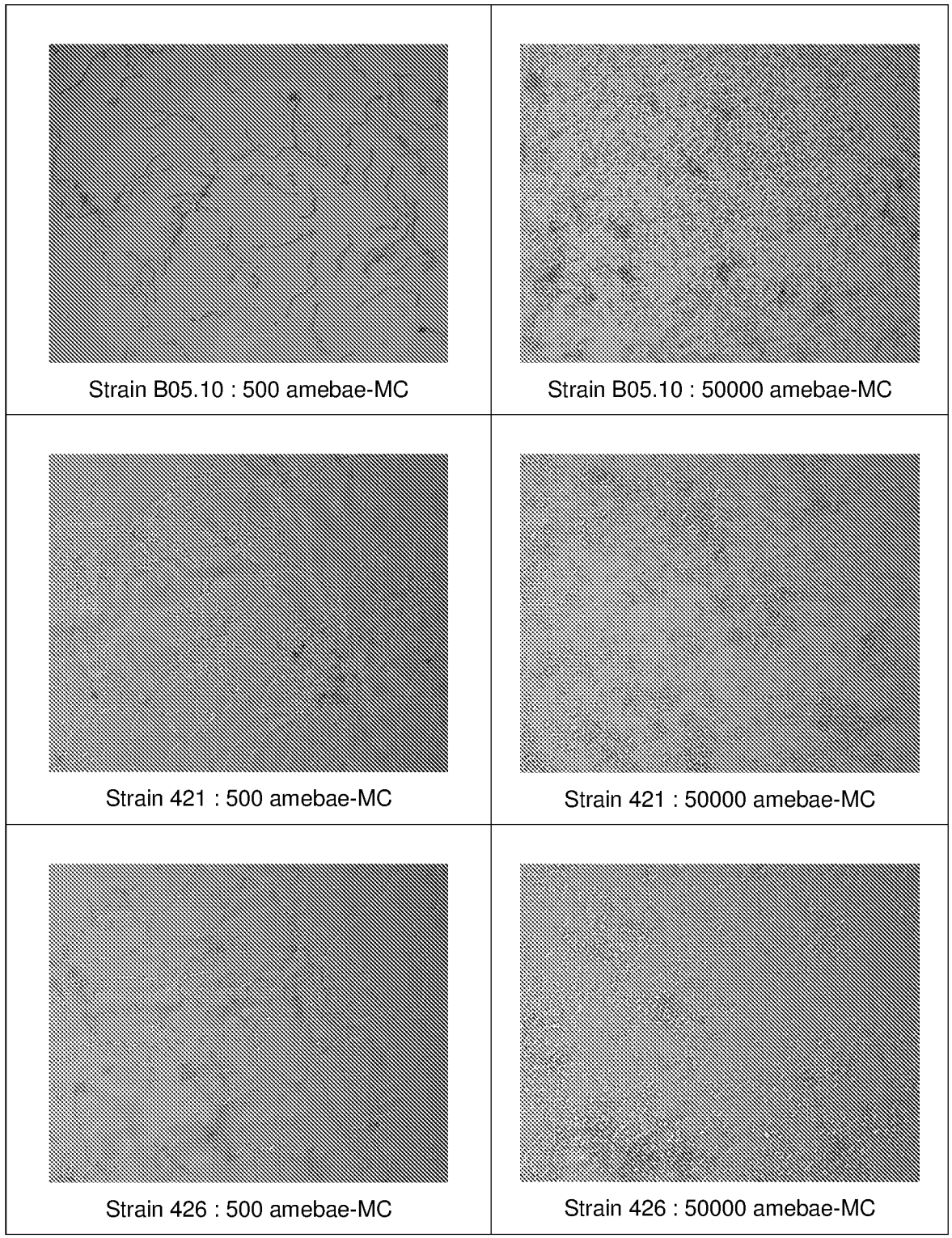
FIG. 2: Effect of the amebae on the germination of *B. cinerea*. Tests in a microplate in the presence of the *B. cinerea* spores+500 amebae in MC medium and *B. cinerea* spores+. Sensitive strains: B05.10 and M421. Resistant strain: M426. (respiration-inhibiting fungicide). 50 000 amebae in MC medium. Observation after 24 H of incubation.
Figure 3:
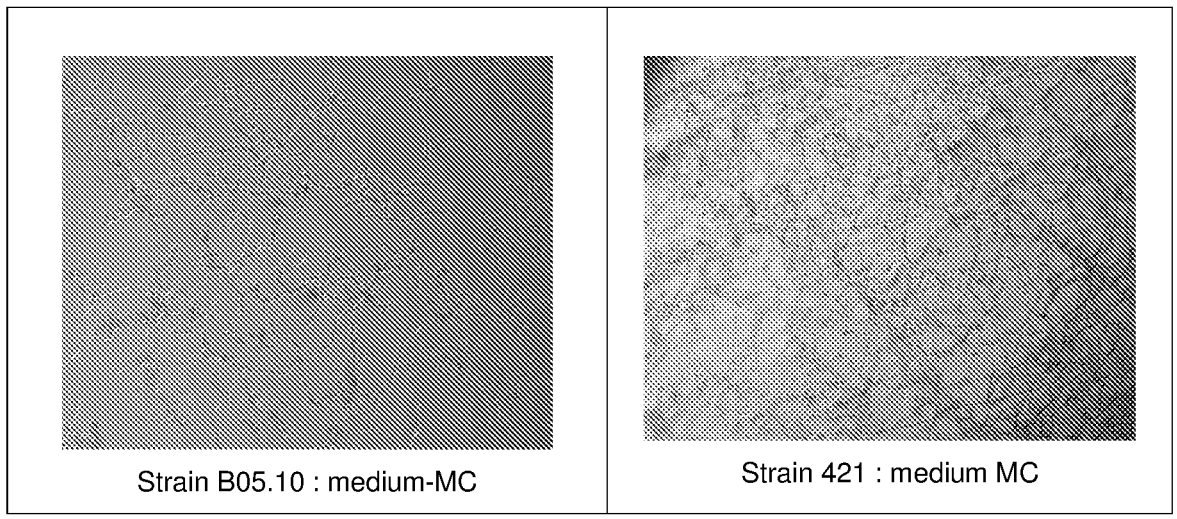
FIG. 3: Effect of the culture medium (MC) on the germination of *B. cinerea* sensitive strains. Tests in a microplate in the presence of the *B. cinerea* spores+culture medium (MC). Sensitive strains: B05.10 and M421. Observation after 24 H of incubation.

Results and conclusion: The observation of the spores after 24 H made it possible to demonstrate a slowing of the germination of the fungus at high amebae concentrations. Regardless of the *B. cinerea* strain, this effect is much more visible when the fungus is in contact with amounts of amebae forming a confluent layer (FIG. 2). With lower ratios (500 amebae) the effect is less visible compared to the controls (FIG. 1 and FIG. 2). The B05.10 strain is a collection strain and it is less vigorous/lively. Compared to the wild-type strains (taken in the field), it will take more time to develop. The culture medium (MC) alone does not affect the growth of the fungus, the culture medium even appears to stimulate the germination of the *B. cinerea* spores (FIG. 3).

These results show an efficacy of *Willaertia magna* on the germination of *B. cinerea* under the experimental conditions, with a qualitative dose effect observed.

Example 3: Efficacy of *Willaertia magna* on Vine (*P. viticola*) Downy Mildew Principle: the tests are carried out on young Cabernet sauvignon plants. Each group of plants is treated under control conditions with a pump sprayer. After treatment of the plants with the solutions tested, an intentional infection of the plants with vine downy mildew is carried out. After 7 to 10 days of incubation, the seriousness of the disease is evaluated in order to evaluate the efficacy of various products with respect to the seriousness of the disease on the nontreated plants.

Protocol:

The cuttings of Cabernet sauvignon plants are produced in a greenhouse (temperature 15° C.-30° C.) and six groups of six plants are formed for the study of each test condition.

The *Willaertia magna* cells are cultured in a culture medium until the desired concentration of $9\times10^9$ cells per liter is obtained.

Various samples are tested:
1. Negative control, condition 1: without treatment.
2. Control of the medium, condition 2: dilution medium
3. Fungicide, condition 3: *Willaertia magna* in culture medium
4. Fungicide, condition 4: sample of condition 3, diluted in dilution medium
5. Fungicide, condition 5: a sample of condition 3 is placed under mechanical stress to kill the *Willaertia* cells. The sample is passed under pressure through a virtually closed, strong-vacuum valve by means of a pump, leading to the death of some of the cells and the lysis of some of the dead cells. The sample obtained is observed under a microscope, with a non-viability label (Trypan blue) in order to count the remaining live cells (not labeled with Trypan blue)
6. Fungicide, condition 6: a sample of condition 4 is placed under mechanical stress to kill the *Willaertia* cells. The sample is passed under pressure through a virtually closed, strong-vacuum valve by means of a pump, leading to the death of some of the cells and the lysis of some of the dead cells. The sample obtained is observed under a microscope, with a non-viability label (Trypan blue) in order to count the remaining live cells (not labeled with Trypan blue)
7. Positive control, condition 6: bordeaux mixture equivalent to 3 kg/ha.

Each sample is applied on one of the groups of six plants by spraying on the whole plant.

24 hours later, a suspension of *P. viticola* sporanges is sprayed on the lower face of the leaves. The plants are then incubated at 24±5° C., illuminated for 14 hours per day, in individual chambers at a humidity favorable to the development of the disease. After 7 to 10 days, an evaluation of the fungicide efficacy under each condition is carried out, for each plant and each leaf stage. The evaluation is based on visual observations of the fungal lesion, consisting of two elements: the infected surface area and the intensity of the sporulation. A scale of 0 to 100% (in 5% increments) is used; each leaf being observed individually. The efficacy is calculated according to the following formula: efficacy=100× [(NT−T)/NT] (NT being the average degree of attack on the nontreated plants and T the average degree of attack on the treated plants). The results are presented in table 2.

TABLE 2

Test conditions and efficacy results

| Condition | Treatment with: | *Willaertia magna* concentration | Volume sprayed (ml) | Average degree of attack of the downy mildew | Fungicide efficacy |
|---|---|---|---|---|---|
| 1 | Negative control: nontreated | 0 | 175 | 56.3% | 0% |
| 2 | Control: *Willaertia magna* dilution medium | 0 | 160 | 55.0% | 2.2% |
| 3 | $9.02 \times 10^9$ live *Willaertia magna*/liter in culture medium | $9.02 \times 10^9$ live *Willaertia magna*/liter | 190 | 1.3% | 97.8% |
| 4 | Condition 3 diluted in *Willaertia magna* dilution medium | $2.80 \times 10^9$ live *Willaertia magna*/liter | 200 | 2.5% | 95.6% |
| 5 | Condition 3 + mechanical inactivation | At least 80% of dead cells compared to condition 3 | 175 | 1.3% | 97.8% |
| 6 | Condition 4 + mechanical inactivation | At least 96% of dead cells compared to condition 4 | 185 | 30.0% | 46.7% |
| 7 | Positive control: bordeaux mixture (equivalent 3 kg/ha) | 0 | 180 | 0.0% | 100% |

Results and conclusion: the severity of the disease is high (56.3%) on the nontreated plants. This value is also high (55%) after spraying the dilution medium.

A very small amount of disease is observed on the plants treated with *Willaertia magna*, in live form: the infection with *P. viticola* is 2.5 to 1.3% of the surface area of the leaves (compared with 56% for the nontreated negative control). That is to say an efficacy of more than 95%, close to the efficacy of the reference fungicide (bordeaux mixture at 3 kg/ha) which enables a complete control of vine downy mildew with an efficacy of 100% (no downy mildew attack).

A small amount of disease is observed on the plants treated with *Willaertia magna* in dead form, inactivated by mechanical action by passing through a pump and strong-vacuum valve: the infection with *P. viticola* is from 30% to only 1.3% of the surface area of the leaves (compared with 56% for the nontreated negative control).

In conclusion, *Willaertia magna*, in live form and in dead form, provides a high activity against vine downy mildew under the experimental conditions.

The invention claimed is:

1. A method for combating proliferation of fungi, excluding treatment methods applied to a human or animal body, comprising a step of bringing protozoa of *Willaertia magna* species into contact with said fungi, wherein the protozoa of the *Willaertia magna* species are used in dead cell lysate form.

2. The method as claimed in claim 1, wherein the protozoa correspond to a strain deposited under number PTA-7824 at ATCC.

3. The method as claimed in claim 1, for combating the proliferation of parasitic fungi of plants.

4. The method as claimed in claim 3, for treating fungal diseases of vine, of cereals, of potatoes, of fruit trees and of market garden crops.

5. The method as claimed in claim 1, (i) for disinfecting networks of air treatment facilities, (ii) for combating fungal contaminations and/or formation of fungal biofilms in food products, food product transformation/production equipment, food product transformation/production factories or cosmetic products, surfaces that come into contact with food products or cosmetic products, or (iii) for treating contaminations of interior environments.

6. The method as claimed in claim 3, wherein the parasitic fungi is chosen from *B. cinerea, E. necator, F. solani, C. globosum, P. chrysogenum, P. viticola, P. infestans, T. viride, T. harzianum, A. fumigatus, A. alternata, A. flavus, P. variotii, A. niger, C. albicans, U. botrytis, E. nigrum, B. cinerea, P. roqueforti, C. cladosporioides, E. chevalieri, A. pullulans* and a combination thereof.

7. The method of claim 4, wherein the fungal disease is selected from the group consisting of vine powdery mildew, vine downy mildew, cereal *septoria* disease, fusaria disease, cereal net blotch, potato downy mildew, early blight, apple tree scab, *sclerotinia* stem rot of rape, *sclerotinia* stem rot of vegetable crops and combinations thereof.

* * * * *